United States Patent
Huang et al.

(10) Patent No.: US 10,065,942 B2
(45) Date of Patent: Sep. 4, 2018

(54) CRYSTALLINE (2S)-3-[(3S,4S)-3-[(1R)-1-HYDROXYETHYL]-4-(4-METHOXY-3-{[1-(5-METHYLPYRIDIN-2-YL)AZETIDIN-3-YL]OXY}PHENYL)-3-METHYLPYRROLIDIN-1-YL]-3-OXOPROPANE-1,2-DIOL

(71) Applicant: Eli Lilly and Company, Indianapolis, IN (US)

(72) Inventors: Ping Huang, Indianapolis, IN (US); Seth Dietrich Ribe, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/505,740

(22) PCT Filed: Aug. 28, 2015

(86) PCT No.: PCT/US2015/047415
§ 371 (c)(1),
(2) Date: Feb. 22, 2017

(87) PCT Pub. No.: WO2016/036596
PCT Pub. Date: Mar. 10, 2016

(65) Prior Publication Data
US 2017/0233373 A1    Aug. 17, 2017

(30) Foreign Application Priority Data

Sep. 4, 2014    (WO) ................ PCT/CN2014/085925

(51) Int. Cl.
*C07D 401/14* (2006.01)
*A61K 31/4439* (2006.01)
*A61K 31/4985* (2006.01)

(52) U.S. Cl.
CPC ........ *C07D 401/14* (2013.01); *A61K 31/4439* (2013.01); *A61K 31/4985* (2013.01); *C07B 2200/13* (2013.01)

(58) Field of Classification Search
CPC ........................... C07D 401/14; A61K 31/4985
See application file for complete search history.

(56) References Cited

U.S. PATENT DOCUMENTS 9,034,864 B2    5/2015    Huang et al.
9,266,859 B2    2/2016    Deng

FOREIGN PATENT DOCUMENTS

| EP | 2564849 A1 | 3/2013 |
|---|---|---|
| WO | 01/47905 A1 | 7/2001 |
| WO | 2007/039075 A2 | 4/2007 |
| WO | 2014/159012 A2 | 10/2014 |

OTHER PUBLICATIONS

Yasuhiro Kaiho, et al., "The effects of type 4 phosphodiesterase inhibitor and the muscarinic cholinergic antagonist tolterodine tartrate on detrusor overactivity in female rats with bladder outlet obstruction." Journal Compilation, 2007, BJU International, 101, 615-620.

Paul J Nichols, et al., "Preparation of Pyrrolidine-Based PDE4 Inhibitors via Enantioselective Conjugate Addition of a-Substituted Malonates to Aromatic Nitroalkenes.", Organic Letters, 2006, vol. 8, No. 7, 1495-1498.

*Primary Examiner* — Andrew D Kosar
*Assistant Examiner* — John S Kenyon
(74) *Attorney, Agent, or Firm* — Danny L. Wood

(57) ABSTRACT

The invention provides crystalline (2S)-3-[(3S,4S)-3-[(1R)-1-hydroxyethyl]-4-(4-methoxy-3-{[1-(5-methylpyridin-2-yl)azetidin-3-yl]oxy}phenyl)-3-methylpyrrolidin-1-yl]-3-oxopropane-1,2-diol, and pharmaceutical compositions thereof. The invention further provides methods of using this compound to treat overactive bladder.

2 Claims, No Drawings

CRYSTALLINE (2S)-3-[(3S,4S)-3-[(1R)-1-HYDROXYETHYL]-4-(4-METHOXY-3-{[1-(5-METHYLPYRIDIN-2-YL)AZETIDIN-3-YL]OXY}PHENYL)-3-METHYLPYRROLIDIN-1-YL]-3-OXOPROPANE-1,2-DIOL

The invention provides crystalline (2S)-3-[(3S,4S)-3-[(1R)-1-hydroxyethyl]-4-(4-methoxy-3-{[1-(5-methylpyridin-2-yl)azetidin-3-yl]oxy}phenyl)-3-methylpyrrolidin-1-yl]-3-oxopropane-1,2-diol, pharmaceutical compositions thereof, methods of using the same, and processes for preparing the same.

Overactive bladder (OAB) is a symptomatically defined medical condition referring to the symptoms of urinary frequency and urgency, with or without urge incontinence. OAB is a condition that adversely affects the quality of life and social functioning of approximately 17 percent of the adult population. In spite of progress made for OAB treatment, many patients suffer with OAB for years without resolution. The first-line treatment for OAB are antimuscarinic drugs which have a good initial response, but experience diminishing patient compliance over the long term due to adverse effects and decreasing efficacy. There remains a significant unmet need for safe and effective OAB treatments.

Cyclic nucleotides (cAMP and cGMP) are important secondary messengers that modulate the contractility of smooth muscle. Cyclic nucleotide phosphodiesterases (PDEs) hydrolyse cyclic nucleotides and are important in regulating the level and duration of action of cyclic nucleotides inside cells. Compounds which inhibit PDE elevate cellular levels of cyclic nucleotides and thereby relax many types of smooth muscle. Previous studies have shown that relaxation of bladder smooth muscle is mainly mediated by agents that elevate cAMP. Phosphodiesterase 4 (PDE4) is cAMP specific and abundantly expressed in bladder. As such, PDE4 has been implicated in the control of bladder smooth muscle tone in vitro and in animal models of overactive bladder (Kaiho, Y. et al. *BJU International* 2008, 101(5), 615-620).

The compounds of the present invention are inhibitors of phosphodiesterase 4 (PDE4) and demonstrate selectivity for PDE4. As such, compounds of the present invention are believed to be useful for the treatment of conditions in which PDE4 plays a role such as overactive bladder, including relief of associated symptoms such as frequency and urgency. Further, the present invention, a crystalline form of (2S)-3-[(3S,4S)-3-[(1R)-1-hydroxyethyl]-4-(4-methoxy-3-{[1-(5-methylpyridin-2-yl)azetidin-3-yl]oxy}phenyl)-3-methylpyrrolidin-1-yl]-3-oxopropane-1,2-diol, is believed to provide advantages in processing, handling, or manufacturability.

International Application Publication WO 01/47905 discloses certain pyrrolindine derivative compounds as inhibitors of phosphodiesterase, in particular, PDE4, and recites the compounds as useful in treating a number of diseases including asthma.

The present invention provides novel compounds which are inhibitors of PDE4 and as such, are useful in treatment of overactive bladder and other disorders. The compounds provided address the need for safe and effective treatments of conditions associated with PDE4 such as overactive bladder.

The present invention provides a compound of formula I

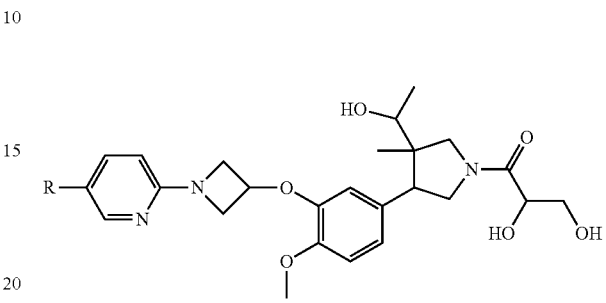

wherein R is hydrogen or methyl, or a pharmaceutically acceptable salt thereof.

A particular compound of formula I is one wherein R is methyl or a pharmaceutically acceptable salt thereof.

A particular compound of formula I is (2S)-3-[(3S,4S)-3-[(1R)-1-hydroxyethyl]-4-(4-methoxy-3-{[1-(5-methylpyridin-2-yl)azetidin-3-yl]oxy}phenyl)-3-methylpyrrolidin-1-yl]-3-oxopropane-1,2-diol, or a pharmaceutically acceptable salt thereof.

Further, the present invention provides crystalline (2S)-3-[(3S,4S)-3-[(1R)-1-hydroxyethyl]-4-(4-methoxy-3-{[1-(5-methylpyridin-2-yl)azetidin-3-yl]oxy}phenyl)-3-methylpyrrolidin-1-yl]-3-oxopropane-1,2-diol.

Further, the present invention provides crystalline (2S)-3-[(3S,4S)-3-[(1R)-1-hydroxyethyl]-4-(4-methoxy-3-{[1-(5-methylpyridin-2-yl)azetidin-3-yl]oxy}phenyl)-3-methylpyrrolidin-1-yl]-3-oxopropane-1,2-diol characterized by an X-ray powder diffraction pattern using CuKα radiation having a diffraction peak at diffraction angle 2-theta of 18.50 in combination with one or more of the peaks selected from the group consisting of 16.2°, 20.2°, and 14.4°; with a tolerance for the diffraction angles of 0.2 degrees.

Further, the present invention provides a pharmaceutical composition comprising a compound of formula I, or a pharmaceutically acceptable salt thereof, and a pharmaceutically acceptable carrier, diluent or excipient. In a particular embodiment, the pharmaceutical composition further comprises one or more other therapeutic agents such as tadalafil. As such, the present invention provides a pharmaceutical composition comprising a first component which is a compound of formula I, or a pharmaceutically acceptable salt thereof, and a second component which is tadalafil, and a pharmaceutically acceptable carrier, diluent or excipient.

Further, the present invention provides a compound of formula I, or a pharmaceutically acceptable salt thereof, for use in therapy.

Further, the present invention provides a compound of formula I, or a pharmaceutically acceptable salt thereof, for use in the treatment of overactive bladder.

Further, the present invention provides the use of a compound of formula I, or a pharmaceutically acceptable salt thereof, for the manufacture of a medicament for treating overactive bladder.

A particular compound of formula I is a compound of formula Ia

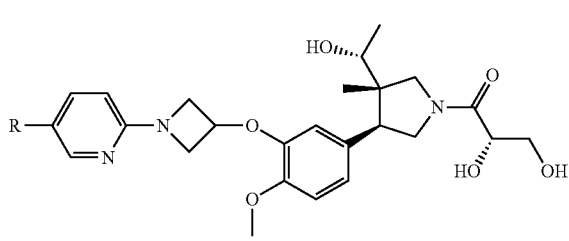

wherein R is hydrogen or methyl, or a pharmaceutically acceptable salt thereof.

A particular compound of formula Ia is one wherein R is methyl, or a pharmaceutically acceptable salt thereof.

A particular compound of formula Ia is (2S)-3-[(3S,4S)-3-[(1R)-1-hydroxyethyl]-4-(4-methoxy-3-{[1-(5-methylpyridin-2-yl)azetidin-3-yl]oxy}phenyl)-3-methylpyrrolidin-1-yl]-3-oxopropane-1,2-diol, or a pharmaceutically acceptable salt thereof.

Further, the present invention provides a method of treating overactive bladder, comprising administering to a patient in need thereof an effective amount of a compound of formula Ia, or a pharmaceutically acceptable salt thereof. In a particular embodiment, the invention provides a method of treating overactive bladder, comprising administering to a patient in need thereof an effective amount of a first component which is a compound of formula Ia, or a pharmaceutically acceptable salt thereof, in combination with an effective amount of a second component which is tadalafil.

Further, the present invention provides a compound of the invention for simultaneous, separate or sequential use in combination with tadalafil in the treatment of overactive bladder.

Further, the invention provides a method of treating overactive bladder comprising administrating to a patient in need thereof an effective amount of (2S)-3-[(3S,4S)-3-[(1R)-1-hydroxyethyl]-4-(4-methoxy-3-{[1-(5-methylpyridin-2-yl)azetidin-3-yl]oxy}phenyl)-3-methylpyrrolidin-1-yl]-3-oxopropane-1,2-diol, or a pharmaceutically acceptable salt thereof, in combination with an effective amount of tadalafil.

It is understood that compounds of the present invention may exist as stereoisomers. Embodiments of the present invention include all enantiomers, diastereomers, and mixtures thereof. Preferred embodiments are single diastereomers, and more preferred embodiments are single enantiomers.

The term "pharmaceutically acceptable salt" includes an acid addition salt that exists in conjunction with the basic portion of a compound of formula I. Such salts include the pharmaceutically acceptable salts, for example those listed in Handbook of Pharmaceutical Salts: Properties, Selection and Use, P. H. Stahl and C. G. Wermuth (Eds.), Wiley-VCH, New York, 2002 which are known to the skilled artisan.

In addition to pharmaceutically acceptable salts, other salts are contemplated in the invention. They may serve as intermediates in the purification of compounds or in the preparation of other pharmaceutically-acceptable salts, or are useful for identification, characterization or purification of compounds of the invention.

As used herein, the term "patient" refers to a warm blooded animal such as a mammal and includes a human. A human is a preferred patient.

It is also recognized that one skilled in the art may treat overactive bladder by administering to a patient presently displaying symptoms an effective amount of the compound of formula I. Thus, the terms "treatment" and "treating" are intended to refer to all processes wherein there may be a slowing, interrupting, arresting, controlling, or stopping of the progression of an existing disorder and/or symptoms thereof, but does not necessarily indicate a total elimination of all symptoms.

It is also recognized that one skilled in the art may treat overactive bladder by administering to a patient at risk of future symptoms an effective amount of the compound of formula I and is intended to include prophylactic treatment of such.

As used herein, the term "effective amount" of a compound of formula I refers to an amount, that is a dosage, which is effective in treating a disorder, such as overactive bladder described herein. The attending diagnostician, as one skilled in the art, can readily determine an effective amount by the use of conventional techniques and by observing results obtained under analogous circumstances. In determining an effective amount or dose of a compound of formula I, a number of factors are considered, including, but not limited to the compound of formula I to be administered; the co-administration of other agents, if used; the species of mammal; its size, age, and general health; the degree of involvement or the severity of the disorder, such as overactive bladder; the response of the individual patient; the mode of administration; the bioavailability characteristics of the preparation administered; the dose regimen selected; the use of other concomitant medication; and other relevant circumstances.

A compound of formula I may be used in combination with other drugs that are used in the treatment/prevention/suppression or amelioration of the diseases or conditions for which compounds of formula I are useful, including overactive bladder. Such other drug(s) may be administered by a route and in an amount commonly used therefore, including contemporaneously or sequentially with a compound of formula I. When a compound of formula I is used contemporaneously with one or more other drugs, a pharmaceutical unit dosage form containing such other drugs in addition to the compound of formula I is preferred. Accordingly, the pharmaceutical compositions of the present invention include those containing one or more other active ingredients in addition to a compound of formula I. Other active ingredients effective in the treatment of overactive bladder which may be combined with a compound of formula I, either administered separately or in the same pharmaceutical include an inhibitor of PDE5 such as tadalafil.

The compounds of the present invention can be administered alone or in the form of a pharmaceutical composition combined with pharmaceutically acceptable carriers or excipients, the proportion, and nature of which are determined by the solubility and chemical properties, including stability, of the compound selected, the chosen route of administration, and standard pharmaceutical practice. The compounds of the present invention, while effective themselves, may also be formulated and administered in the form of their pharmaceutically acceptable salts for convenience of crystallization, increased solubility, and the like.

One skilled in the art of preparing formulations can readily select the proper form and mode of administration depending upon the particular characteristics of the compound selected, the disorder or condition to be treated, the stage of the disorder or condition, and other relevant circumstances (See, e.g., Remington: The Science and Practice of Pharmacy, D. B. Troy, Editor, 21st Edition., Lippincott, Williams & Wilkins, 2006).

PDE4 Inhibition In Vitro Assay

The phosphodiesterase assays are performed essentially according to the method described in Loughney, K., et al., *J. Biol. Chem.*, 271, pp. 796-806 (1996). PDE4A, PDE4B, PDE4C, PDE4D, and PDE5 human recombinant proteins are expressed and purified from *Saccharomyes cerevisiae* that lack endogenous PDEs. The phosphodiesterase enzymes are diluted on ice with enzyme dilution buffer (25 mM Tris, pH 7.5, 0.1 mM DTT, 5.0 mM $MgCl_2$, 100 mM NaCl, 5 µM $ZnSO_4$, 100 µg/mL BSA) to give approximately 20%-40% hydrolysis of cyclic nucleotide monophosphate (cNMP) in the absence of inhibitor.

The stock solution of test compounds are diluted on the Beckman BioMek™ 1000 workstation to span a concentration range of 4.5 log units in 0.5 log increments. The DMSO concentration in the final test system is 2.5% for all PDE enzymes. The final test compound concentration tested ranged from 0.03 nM to 1 µM.

The assay is performed in a 96-well microtiter plate format on a Beckman BioMek™ 1000 robotic station. Each row of the plate represents a 10-point dose response curve containing blank (no enzyme), non-inhibited control, and inhibitor dilutions spanning 4.5 log units in concentration in 0.5 log increments. Assay stock solutions are loaded into the Biomek reservoirs (water, inhibitor diluent [2.5% or 10% DMSO], 5×PDE assay buffer, substrate, inhibitor solutions, enzyme solutions, snake venom nucleotidase, and charcoal suspension). The reaction is initiated with enzyme, and incubated for 15 minutes at 30° C. An excess of *Crotalus atrox* snake venom nucleotidase (5 µL/well) is then added and the mixture is incubated for an additional 3 minutes. The reaction is terminated by the addition of 200 µL of activated charcoal suspension, after which the plate is centrifuged for 5 minutes at 750×g. A transfer program is run in which 200 µL of supernatant is removed and placed into a new plate. The amount of radioactivity released as phosphate is determined in a Wallac MicroBeta Plate™ counter.

The reduced data at each concentration of inhibitor is analyzed using a four-, three- or two-parameter logistic dose response model to provide an $IC_{50}$ value. For those sets of data that exhibited >95% inhibition at the maximal inhibitor concentration, a four-parameter logistic dose response model is used.

In the above assay, the compounds Examples 1 and 2 exhibit an $IC_{50}$ of less than 10 nM at PDE4B. More specifically, the compound of Example 2 has an $IC_{50}$ of 0.58 nM measured at PDE4B in the above assay. These data demonstrate the compounds of Example 1 and 2 are inhibitors of PDE4B.

Overactive Bladder In Vivo Model

The in vivo effect of PDE4 inhibitors on OAB is studied with a chronic cyclophosphamide (CYP)-induced overactive bladder mouse model adapted from Boudes et al., *Neurourol. Urodynam.* 2011. In a typical study, female C57/Bl6 mice, approximately 20 grams in body weight (Harlan Laboratories, Inc., Indianapolis, Ind.) are used. Mice are randomized by body weight into groups one day before the start of the study. Mice are individually housed and maintained on a 12 hour light/dark cycle at 22° C. with ad lib access to food (TD 2014 with 0.72% Ca and 0.61% P, 990 IU/g D3, Teklad™, Madison, Wis.) and water. Animals receive cyclophosphamide (dissolved in physiological saline) i.p. administration at 100 mg/kg on days 1, 3, 5, and 7 to chronically induce OAB. The vehicle control group received daily vehicle (HEC 1%/Tween 80 0.25%/Antifoam 0.05%) administered orally. All other groups are administered orally tadalafil at 10 mg/kg in combination with 0.1, 1.0, or 10.0 mg/kg of test compound daily at a volume of 200 µL/mouse. On day 8, mice are housed in urine collection chambers with a filter paper placed underneath chamber. Prior to urine collection, gavages of 1 ml water are given to each mouse. Urine is collected from 6 pm to 10 pm (i.e. for 4 hrs). Gel cups (DietGel™ 76A) are supplied as water source during the 4 hour period. The filter paper is changed every hour. Voiding frequency and volume/void are calculated using Image J software (NIH). Data are statistically analyzed with JMP8® software (Cary, N. C.).

The animals develop OAB after 8 days following CYP treatment as demonstrated by increased urinary frequency (sham: 6.66±0.91 vs. vehicle: 16.5±1.65 number of urination/4 hour period) and decreased volume/void (sham: 173.36±38.39 mL vs. vehicle: 31.93±4.16 mL). All treatment groups receive a fixed dose of 10 mg/kg of tadalafil. At this dose, tadalafil has no significant activity on either urinary frequency or volume per void. Following the protocol essentially as described above, the compound of Example 2 given with tadalafil significantly reduces urinary frequency in a dose-dependent fashion (Table 1). In addition, increases of volume/void are also observed in a dose-dependent fashion (Table 2). This demonstrates that a compound of Example 2 in combination with tadalafil is active in an animal model of overactive bladder.

TABLE 1

| Treatment | Mean Voiding Frequency (no./4 hr) | Standard Error | p value vs. Vehicle* |
|---|---|---|---|
| Vehicle | 16.5 | 1.6583 | |
| Example 2 0.1 mg/kg + tadalafil 10 mg/kg | 10 | 0.9587 | 0.0057 |
| Example 2 1.0 mg/kg + tadalafil 10 mg/kg | 8.61 | 0.7633 | 0.0003 |
| Example 2 10.0 mg/kg + tadalafil 10 mg/kg | 8.38 | 1.2049 | 0.0000 |

*$p < 0.05$ is statistically significant; $p < 0.001$ is statistically highly significant; p-values computed based on ANOVA model for the square root transform of number of spots in 4 hours; p-values adjusted for multiple comparisons to vehicle using Dunnett's correction.

TABLE 2

| Treatment | Mean Volume/ Void (mL) | Standard Error | p value vs. Vehicle* |
|---|---|---|---|
| Vehicle | 31.93 | 4.1635 | |
| Example 2 0.1 mg/kg + tadalafil 10 mg/kg | 47.30 | 6.3428 | 0.29619 |
| Example 2 1.0 mg/kg + tadalafil 10 mg/kg | 77.15 | 5.6815 | 0.00003 |

TABLE 2-continued

| Treatment | Mean Volume/ Void (mL) | Standard Error | p value vs. Vehicle* |
|---|---|---|---|
| Example 2 10.0 mg/kg + tadalafil 10 mg/kg | 81.93 | 10.0205 | 0.00007 |

*$p < 0.05$ is statistically significant; $p < 0.001$ is statistically highly significant; p-values computed based on ANOVA model for the logarithm of urine spot volumes; p-values adjusted for multiple comparisons to vehicle using Dunnett's correction.

Compounds of formula I may be prepared by processes known in the chemical arts or by a novel process described herein. A process for the preparation of a compound of formula I, or a pharmaceutically acceptable salt thereof, and novel intermediates for the manufacture of a compound of formula I, provide further features of the invention and are illustrated by the following procedures in which the meaning of substituent, R is as defined above, unless otherwise specified.

Generally, a compound of formula Ia where R is hydrogen or methyl may be prepared from a compound of formula II where the 1,2-diol group is protected with a suitable group such as acetonide (Scheme 1). More specifically, a compound of formula II is reacted with an acid such aqueous hydrochloric acid or acetic acid in a suitable solvent to provide a compound of formula Ia. Suitable solvents include water, methanol and acetonitrile. A compound of formula II where R is hydrogen or methyl may be prepared by reacting a compound of formula III with a compound of formula IV where L represents a suitable leaving group such as fluoro or chloro in the presence of a suitable base. Suitable bases include potassium carbonate and cesium carbonate. The reaction is conveniently carried out in a solvent such as N-methyl-2-pyrrolidone or acetonitirile.

A compound of formula III may be prepared from a compound of formula V where the azetidine amine is protected with a suitable group such as diphenylmethyl. More specifically, a compound of formula V is reacted with hydrogen gas in the presence of suitable catalyst such as palladium on carbon to provide a compound of formula III. The reaction is conveniently carried out in a solvent such as methanol or ethanol.

A compound of formula V may be prepared by reacting a compound of formula VI with 1-(diphenylmethyl)azetidin-3-yl methanesulfonate in the presence of a suitable base. Suitable bases include potassium carbonate and cesium carbonate. The reaction is conveniently carried out in an appropriate solvent such as acetonitirile.

Scheme 1

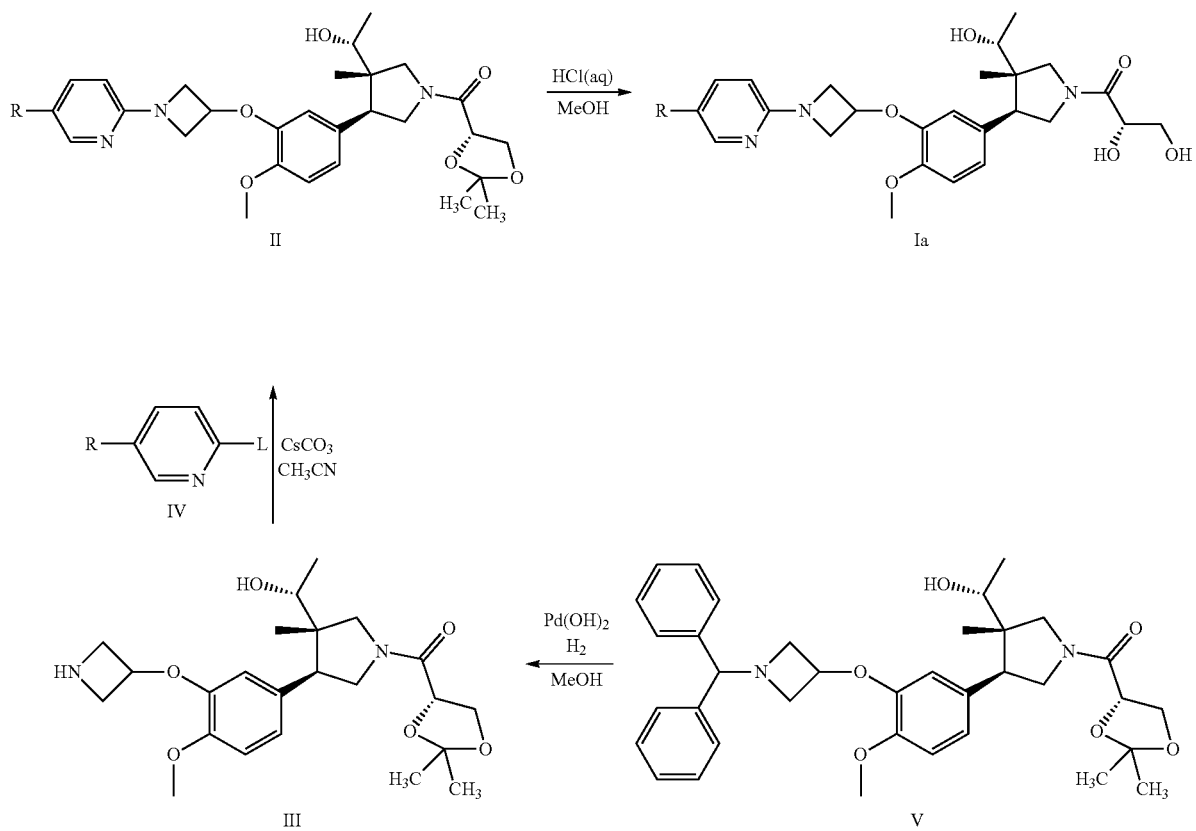

-continued

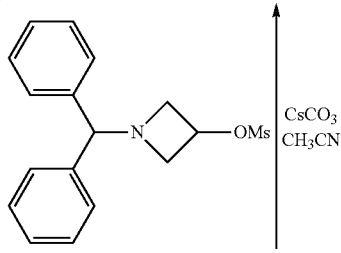

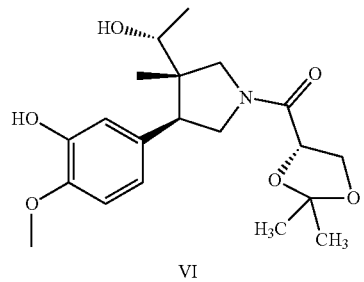

VI

Alternatively, a compound of formula II may be prepared directly from a compound of formula VI (Scheme 2). More specifically, a compound of formula VI is reacted with a compound of formula VII where R is hydrogen or methyl and OMs represents the leaving group methanesulfonyl in the presence of a suitable base such as cesium carbonate. The reaction is conveniently carried out in an appropriate solvent such as acetonitirile.

A compound of formula VII may be prepared by reacting a compound of formula VIII with methanesulfonyl chloride in the presence of a base such as triethylamine. The reaction is conveniently carried out in a suitable solvent such as methylene chloride. A compound of formula VIII where R is hydrogen or methyl may be prepared by reacting a compound of formula IV where L represents a suitable leaving group such as fluoro or chloro with 3-hydroxy azetidine in the presence of a suitable base. Suitable bases include potassium carbonate. The reaction is conveniently carried out in a suitable solvent.

Scheme 2

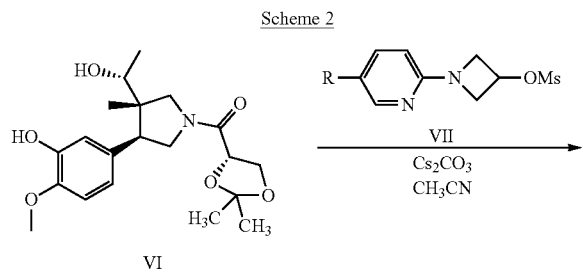

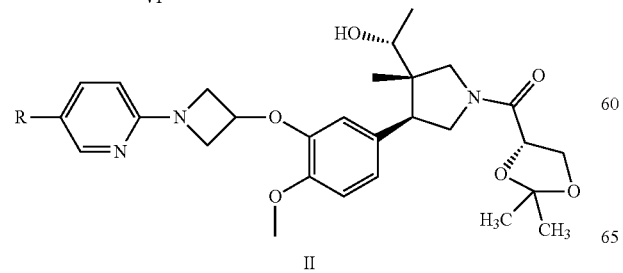

-continued

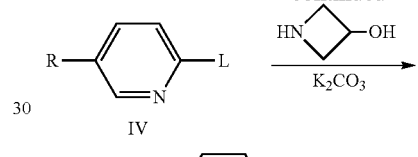

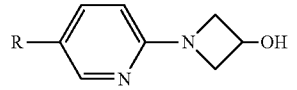

VIII

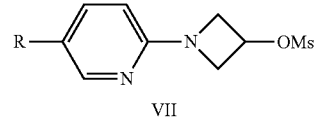

VII

A compound of formula VI may be prepared by procedures appreciated by one of ordinary skill in the art including those disclosed in International Application Publication No. WO 01/47905 as well as those disclosed in Scheme 3 in view of Nichols, P. J.; DeMattei, J. A.; Barnett, B. R.; LeFur, N. A.; Chuang, T.; Piscopio, A. D.; Kock, K. *Org. Lett.* 2006, 8, 1495-1498.

Scheme 3

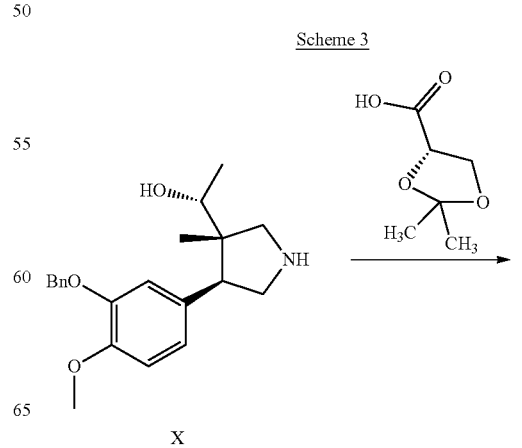

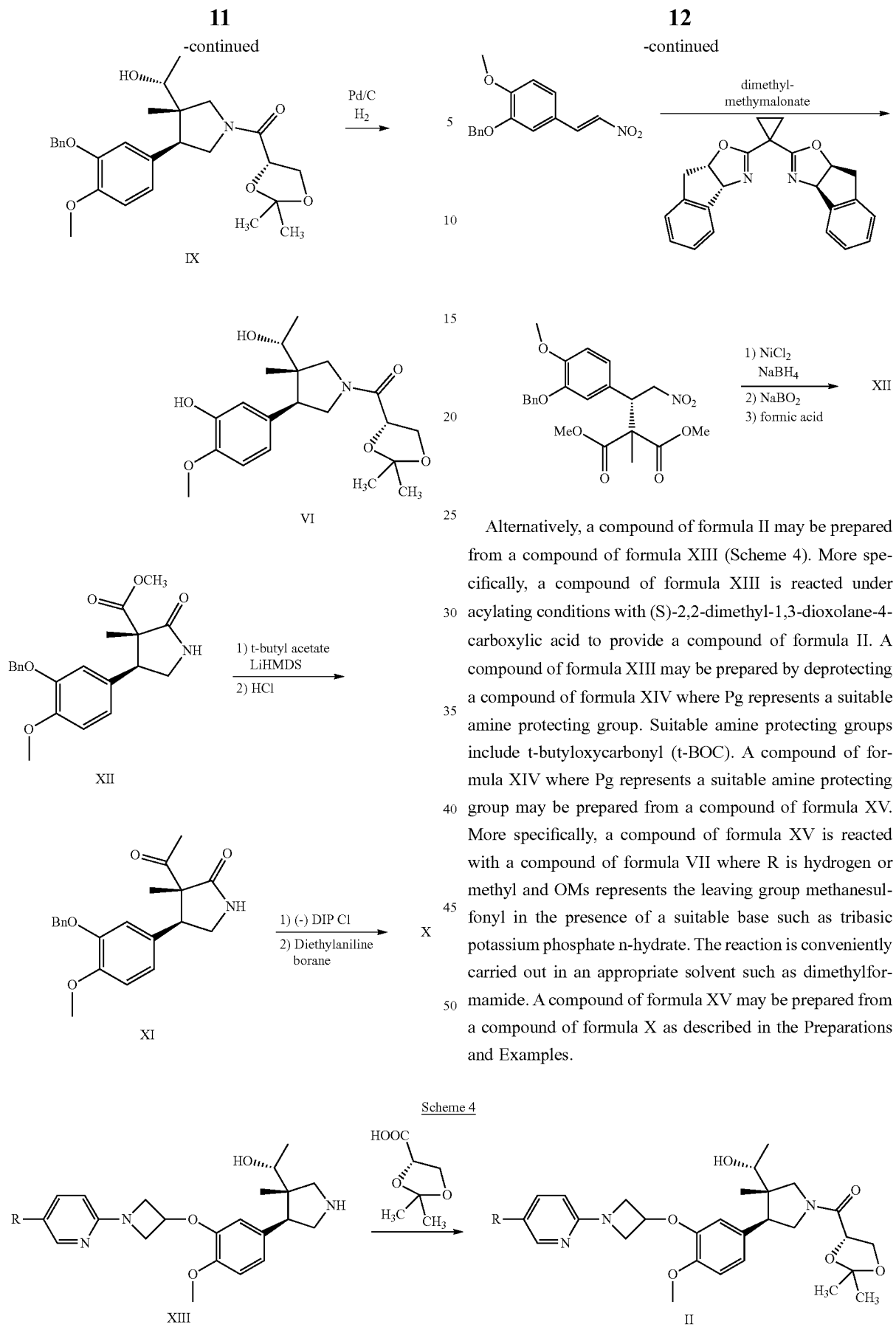

Alternatively, a compound of formula II may be prepared from a compound of formula XIII (Scheme 4). More specifically, a compound of formula XIII is reacted under acylating conditions with (S)-2,2-dimethyl-1,3-dioxolane-4-carboxylic acid to provide a compound of formula II. A compound of formula XIII may be prepared by deprotecting a compound of formula XIV where Pg represents a suitable amine protecting group. Suitable amine protecting groups include t-butyloxycarbonyl (t-BOC). A compound of formula XIV where Pg represents a suitable amine protecting group may be prepared from a compound of formula XV. More specifically, a compound of formula XV is reacted with a compound of formula VII where R is hydrogen or methyl and OMs represents the leaving group methanesulfonyl in the presence of a suitable base such as tribasic potassium phosphate n-hydrate. The reaction is conveniently carried out in an appropriate solvent such as dimethylformamide. A compound of formula XV may be prepared from a compound of formula X as described in the Preparations and Examples.

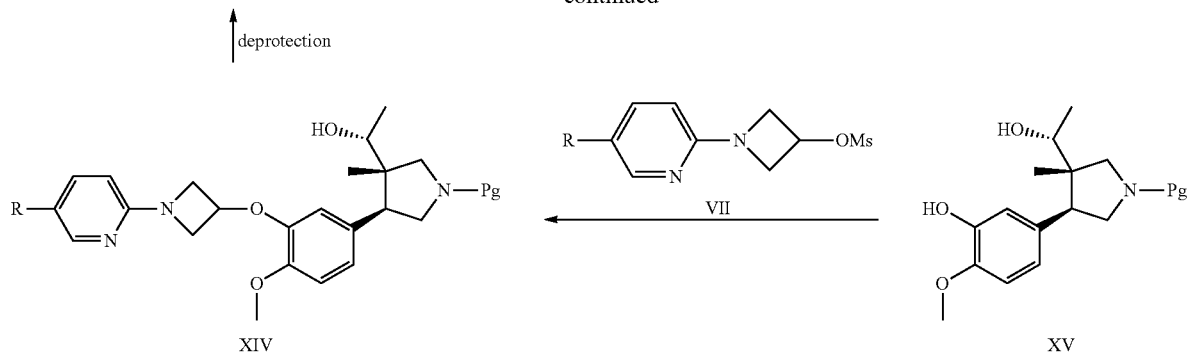

As used herein, "DMSO" refers to dimethylsulfoxide; "Tris" refers to trishydroxymethylaminomethane; "DTT" refers to dithiothreitol; "HEC" refers to hydroxyethyl cellulose; and "$IC_{50}$" refers to the concentration of an agent that produces 50% of the maximal inhibitory response possible for that agent.

It is recognized in the field of organic chemistry that one or more chemical names may be derived for a chemical structure. Alternative names may be presented in the Examples and Preparations.

Preparation 1

Synthesis of (1R)-1-[(3S,4S)-1-{[(4S)-2,2-dimethyl-1,3-dioxolan-4-yl]carbonyl}-4-(3-{[1-(diphenylmethyl)azetidin-3-yl]oxy}-4-methoxyphenyl)-3-methylpyrrolidin-3-yl]ethanol

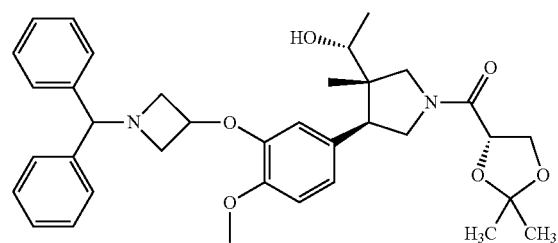 [SMILES: COc1ccc([C@@H]2CN(C(=O)[C@@H]3COC(C)(C)O3)C[C@@]2(C)[C@@H](C)O)cc1OC1CN(C(c2ccccc2)c2ccccc2)C1]

To a suspension of (1R)-1-[(3S,4S)-1-{[(4S)-2,2-dimethyl-1,3-dioxolan-4-yl]carbonyl}-4-(4-methoxy-3-hydroxyphenyl)-3-methylpyrrolidin-3-yl]ethanol (2.0 g) and potassium carbonate (1.46 g) in acetonitrile (30 mL) is added 1-(diphenylmethyl)azetidin-3-yl methanesulfonate (2.51 g). The mixture is heated at 80° C. overnight. Cool the reaction mixture and pour into ethyl acetate (100 mL), wash with water (40 mL) and brine (40 mL), dry over sodium sulfate, filter and evaporate the filtrate to dryness. Purify the resulting residue (silica gel, 60% ethyl acetate/hexanes to ethyl acetate) to provide 0.6 g of the title compound. MS (ES+)=601 (M+1).

Preparation 2

Synthesis of (1R)-1-[(3S,4S)-1-{[(4S)-2,2-dimethyl-1,3-dioxolan-4-yl]carbonyl}-4-(4-methoxy-3-{[1-(azetidin-3-yl]oxy}phenyl)-3-methylpyrrolidin-3-yl]ethanol

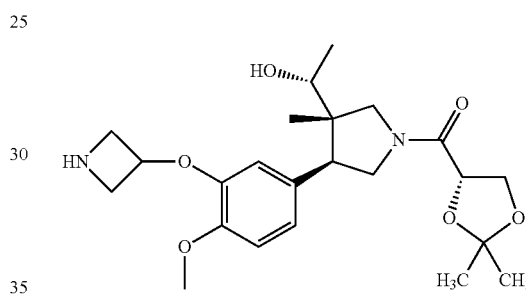

To a Parr™ vessel containing a solution of (1R)-1-[(3S,4S)-1-{[(4S)-2,2-dimethyl-1,3-dioxolan-4-yl]carbonyl}-4-(3-{[1-(diphenylmethyl)azetidin-3-yl]oxy}-4-methoxyphenyl)-3-methylpyrrolidin-3-yl]ethanol (0.6 g) in methanol (20 mL) is added palladium hydroxide on carbon (60 mg, 20 wt % Pd on C dry basis). The suspension is hydrogenated at 30 psig hydrogen gas until hydrogen gas uptake ceases. The reaction mixture is filtered through Celite™ and the filtrate is evaporated to provide the title compound (0.4 g). MS (ES+)=435 (M+1).

Preparation 3

Synthesis of tert-butyl (3S,4S)-4-(3-(benzyloxy)-4-methoxyphenyl)-3-((R)-1-hydroxyethyl)-3-methylpyrrolidine-1-carboxylate

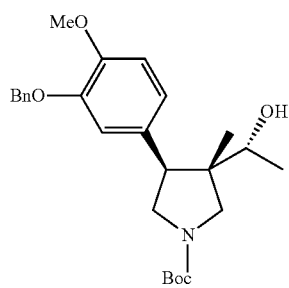

Add triethylamine (0.6 g, 5.93 mmol) to (R)-1-((3S,4S)-4-(3-(benzyloxy)-4-methoxyphenyl)-3-methylpyrrolidin-3-yl)ethan-1-ol (20.0 g, 58.57 mmol) in ethyl acetate (200 mL) Cool the reaction to 0-5° C. Add di-tert-butyl dicarbonate (13.45 g, 61.63 mmol) in methanol (60 mL) to the reaction while maintaining the reaction temperature between 0-5° C. Warm the reaction to 15-20° C. and stir for 2 hours. Add water (200 mL) and separate the layers. Back extract the aqueous layer with ethyl acetate (100 mL). Combine the organic layers and wash with water (100 mL). Concentrate the organic layer to 2 volumes. Add n-heptane (200 mL) and stir at 15-20° C. for 16 hours. Filter the slurry and wash the cake with n-heptane. Dry the cake under vacuum below 50° C. to give the title compound (22.0 g, 49.92 mmol): $^1$H NMR (CDCl$_3$) δ 0.58 (d, J=8.8 Hz, 3H), 1.02 (m, 3H), 1.06 (m, 1H), 1.48 (s, 9H), 3.16 (m, 2H), 3.58 (m, 4H), 3.91 (s, 3H), 5.24 (m, 2H), 6.78 (m, 3H), 7.36 (m, 5H); and $^{13}$C-NMR (CDCl$_3$) δ (ppm) 17.5, 17.6, 19.7, 19.8, 28.8, 45.7, 46.3, 48.4, 48.7, 49.1, 52.4, 52.9, 56.2, 69.1, 71.1, 71.2, 79.5, 111.6, 116.1, 116.3, 121.4, 127.4, 128.0, 128.8, 129.8, 137.8, 147.4, 148.8, 155.2, 155.3. Rotational isomerization is observed in the $^1$H and $^{13}$C spectrum, which is causing doubling of relevant peaks.

Preparation 4

Synthesis of tert-butyl (3S,4S)-3-[(1R)-1-hydroxyethyl]-4-(3-hydroxy-4-methoxyphenyl)-3-methylpyrrolidine-1-carboxylate

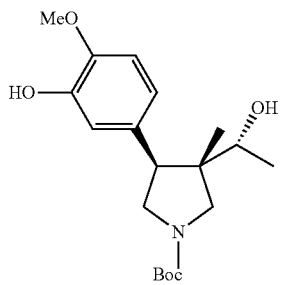 [SMILES: COc1ccc([C@@H]2CN(C(=O)OC(C)(C)C)C[C@@]2(C)[C@@H](C)O)cc1O]

Add palladium hydroxide (0.26 g, 1.85 mmol) to the reaction solution containing tert-butyl (3S,4S)-4-(3-(benzyloxy)-4-methoxyphenyl)-3-((R)-1-hydroxyethyl)-3-methylpyrrolidine-1-carboxylate (5.0 g, 11.32) in methanol (50 mL) and evacuate the reaction to obtain a hydrogen atmosphere of 138-207 kPa at 15-20° C. After two hours, filter the reaction through diatomaceous earth. Wash the filter cake with methanol (10 mL), and concentrate the organic layer to 1-2 volumes. Add MTBE (25 mL), and concentrate the organic to 1-2 volumes. Add additional MTBE (25 mL), and concentrate the organic layer to 1-2 volumes. Add n-heptane (50 mL) to the solution, and stir for sixteen hours at 5-10° C. Filter the slurry, and wash the cake with n-heptanes. Dry the cake under vacuum below 50° C. to give the title compound (3.9 g, 11.10 mmol): $^1$H NMR (CDCl$_3$) δ 0.76 (s, 3H), 1.11 (d, J=6.4 Hz, 3H), 1.48 (s, 9H), 3.24 (m, 2H), 3.60 (m, 5H), 3.88 (s, 3H), 5.62 (brs, 1H), 6.78 (m, 2H), 6.86 (s, 1H); and $^{13}$C-NMR (CDCl$_3$) δ (ppm) 17.6, 17.7, 19.6, 19.7, 28.8, 45.9, 46.1, 46.5, 48.5, 49.1, 49.2, 49.6, 52.7, 53.2, 56.2, 69.3, 79.5, 110.6, 110.7, 115.5, 115.7, 120.6, 120.8, 130.7, 145.5, 145.8, 155.3, 155.4. Rotational isomerization is observed in the $^1$H and $^{13}$C spectrum, which is causing doubling of relevant peaks.

Preparation 5

Synthesis of tert-butyl (3S,4S)-3-((R)-1-hydroxyethyl)-4-(4-methoxy-3-((1-(5-methylpyridin-2-yl)azetidin-3-yl)oxy)phenyl)-3-methylpyrrolidine-1-carboxylate

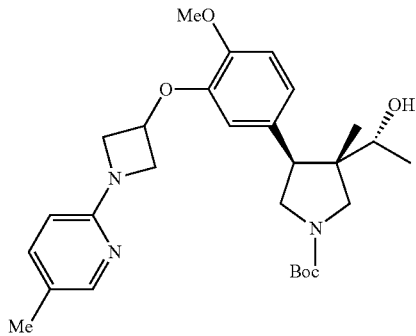 [SMILES: COc1ccc([C@@H]2CN(C(=O)OC(C)(C)C)C[C@@]2(C)[C@@H](C)O)cc1OC1CN(c2ccc(C)cn2)C1]

Add tribasic potassium phosphate n-hydrate (238.1 g, 1.12 mol) to a solution of tert-butyl (3S,4S)-3-[(1R)-1-hydroxyethyl]-4-(3-hydroxy-4-methoxyphenyl)-3-methylpyrrolidine-1-carboxylate (100 g, 274.3 mmol) in dimethylformamide (700 mL). Heat the resulting mixture to 90-95° C. Add a solution of 1-(5-methylpyridin-2-yl)azetidin-3-yl methanesulfonate (73.3 g, 289.81 mmol) in dimethylformamide (30 mL) dropwise to the reaction mixture. After the addition is complete, stir the mixture at 90-100° C. After sixteen hours, cool the reaction to 15-25° C. and add ethyl acetate (2500 mL) and water (2500 mL). Separate the layers and back extract the aqueous layer with ethyl acetate (2500 mL). Combine the organic layers, wash with 12% brine (2500 mL, 2×) and concentrate the organic layer under vacuum under 50° C. to 2-3 volumes. Add tetrahydrofuran (300 mL) and concentrate under vacuum under 50° C. to 2-3 volumes. Add tetrahydrofuran (300 mL) and concentrate under vacuum under 50° C. to 2 volumes. Add tetrahydrofuran (600 mL) to give the title compound (765.7 g, 264.65 mmol) as a solution in tetrahydrofuran, which is used without further purification in the subsequent reaction.

Preparation 6

Synthesis of (R)-1-((3S,4S)-4-(4-methoxy-3-((1-(5-methylpyridin-2-yl)azetidin-3-yl)oxy)phenyl)-3-methylpyrrolidin-3-yl)ethan-1-ol

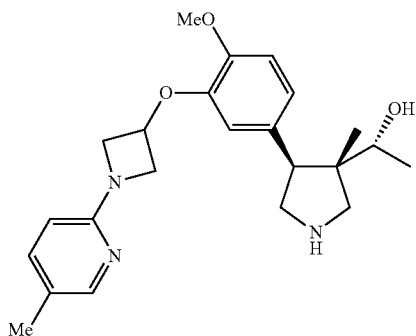 [SMILES: COc1ccc([C@@H]2CNC[C@@]2(C)[C@@H](C)O)cc1OC1CN(c2ccc(C)cn2)C1]

Add concentrated HCl (44 mL, 535.92 mmol, 12.18 M) to a 15-20° C. solution of tert-butyl (3S,4S)-3-((R)-1-hydroxyethyl)-4-(4-methoxy-3-((1-(5-methylpyridin-2-yl)azetidin-3-yl)oxy)phenyl)-3-methylpyrrolidine-1-carboxylate (22.0 g, 44.21 mmol) in tetrahydrofuran (88 mL). After the addition is complete, warm the solution to 30-35° C. After four hours, add 10% aqueous sodium carbonate to adjust the pH to 8-9. Concentrate the reaction until all of the tetrahydrofuran has been removed. Add dichloromethane (440 mL) and separate the layers. Wash the organic layer with water (220 mL). Concentrate the organic layer to obtain the title compound (17.0 g, 42.77 mmol): $^1$H NMR (CDCl$_3$) δ 0.75 (s, 3H), 1.17 (d, J=6.4 Hz, 3H), 2.15 (s, 3H), 3.18 (d, J=11.6 Hz, 1H), 3.47 (s, 2H), 3.65 (m, 2H), 3.79 (m, 6H), 4.07 (m, 2H), 4.50 (m, 2H), 5.10 (t, J=5.2 Hz, 1H), 6.27 (d, J=8.4 Hz, 1H), 6.65 (s, 1H), 6.80 (s, 2H), 7.29 (m, 1H), 7.88 (s, 1H); and $^{13}$C-NMR (CDCl$_3$) δ (ppm) 17.3, 17.8, 19.3, 46.8, 48.0, 49.6, 50.3, 51.1, 55.7, 58.0, 67.5, 68.8, 106.3, 111.5, 114.3, 121.5, 122.0, 128.0, 138.5, 145.9, 146.8, 148.5, 158.6.

Preparation 7

Synthesis of (1R)-1-[(3S,4S)-1-{[(4S)-2,2-dimethyl-1,3-dioxolan-4-yl]carbonyl}-4-(4-methoxy-3-{[1-pyridin-2-ylazetidin-3-yl]oxy}phenyl)-3-methylpyrrolidin-3-yl]ethanol

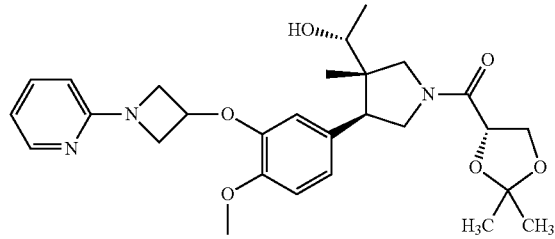 [SMILES: COc1ccc([C@@H]2CN(C(=O)[C@@H]3COC(C)(C)O3)C[C@@]2(C)[C@@H](C)O)cc1OC1CN(c2ccccn2)C1]

A mixture of (1R)-1-[(3S,4S)-1-{[(4S)-2,2-dimethyl-1,3-dioxolan-4-yl]carbonyl}-4-(4-methoxy-3-{[1-(azetidin-3-yl]oxy}phenyl)-3-methylpyrrolidin-3-yl]ethanol (50 mg), 2-fluoropyridine (11.8 mg) and potassium carbonate (31.8 mg) in N-methyl-2-pyrrolidone (3 mL) is heated at 120° C. overnight. The reaction is cooled, poured into methylene chloride (40 mL), and washed with water (10 mL). The organic layer is dried over sodium sulfate and evaporated to 3 mL. Acetonitrile is added and the crude product solution is purified by reverse phase chromatography (5% to 95% acetonitrile/water). The appropriate fractions are collected and evaporated to provide the title compound (22.1 mg). MS (ES+)=512 (M+1).

Preparation 8

Synthesis of (1R)-1-[(3S,4S)-1-{[(4S)-2,2-dimethyl-1,3-dioxolan-4-yl]carbonyl}-4-(4-methoxy-3-{[1-(5-methylpyridin-2-yl)azetidin-3-yl]oxy}phenyl)-3-methylpyrrolidin-3-yl]ethanol

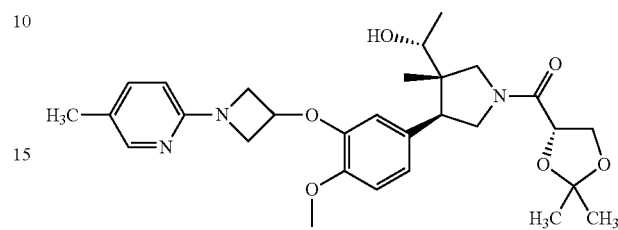

The title compound is prepared essentially by the method of Preparation 7 using 2-chloro-5-methylpyridine. MS(ES+)=526 (M+1).

Alternative synthesis of (1R)-1-[(3S,4S)-1-{[(4S)-2,2-dimethyl-1,3-dioxolan-4-yl]carbonyl}-4-(4-methoxy-3-{[1-(5-methylpyridin-2-yl)azetidin-3-yl]oxy}phenyl)-3-methylpyrrolidin-3-yl]ethanol.

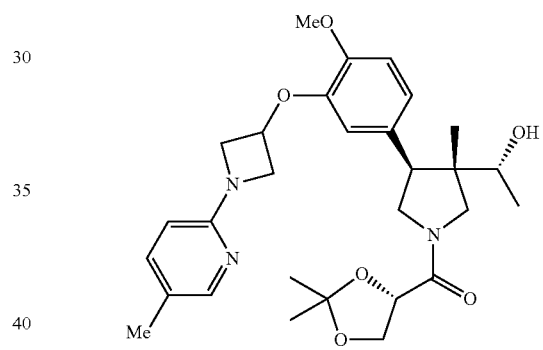

Add potassium (S)-2,2-dimethyl-1,3-dioxolane-4-carboxylate (165 g, 891.13 mmol) to a solution of (R)-1-((3S,4S)-4-(4-methoxy-3-((1-(5-methylpyridin-2-yl)azetidin-3-yl)oxy)phenyl)-3-methylpyrrolidin-3-yl)ethan-1-ol (300 g, 754.68 mmol), dimethylformamide (3000 mL), ethyl acetate (1500 mL) and N-methylmorphine (375 g, 3.71 mol). Cool the mixture to 0-10° C. and stir for thirty minutes. Add a 50 wt % solution of 1-propanephosphonic acid cyclic anhydride (675 g, 1.06 moles, 551.92 mL) in ethyl acetate at an addition rate to maintain the internal temperature between 0-10° C. After stirring at 0-10° C. for thirty minutes, warm the mixture to 10-20° C. After one hour, add water (6.0 L) and ethyl acetate (4.5 L). Separate the layers and back extract the aqueous layer with ethyl acetate (3.0 L). Wash the combined organic layers with water (3.0 L) and concentrate to 3 volumes. Add isopropyl acetate (1.5 L) and concentrate the organic to 3 volumes. Add isopropyl acetate (1.5 L) and stir for twenty hours at 15-20° C. Filter the slurry and dry the solid under vacuum to yield the title compound (290.0 g, 551.7 mmol): $^1$H NMR (CDCl$_3$) δ 0.76 (s, 3H), 1.20 (d, J=6.4 Hz, 3H), 1.45 (m, 6H), 2.20 (s, 3H), 3.75 (m, 3H), 3.85 (m, 6H), 4.20 (m, 4H), 4.42 (m, 3H), 4.68 (m, 1H), 5.10 (m, 1H), 6.30 (d, J=8.4 Hz, 1H), 6.65 (d, J=12.8 Hz, 1H), 6.85 (d, J=2.4 Hz, 2H), 7.30 (d, J=8.4 Hz, 1H), 7.98 (s, 1H); and $^{13}$C-NMR (CDCl$_3$) δ (ppm) 16.9, 17.4, 17.5, 19.6, 21.7, 25.5, 25.6, 25.8, 44.6, 46.3, 47.0, 48.8, 49.3, 49.6, 52.6, 53.0, 55.8, 58.0, 66.4, 67.8, 68.5, 74.1, 74.2, 106.0, 110.6, 111.5, 114.7, 115.0, 121.6, 121.7, 122.1, 122.2, 129.0, 129.6, 138.2, 145.8, 147.5, 147.6, 148.3, 148.4, 158.9, 168.2, 168.4. Rotational isomerization is observed in the $^1$H and $^{13}$C spectrum, which is causing doubling of relevant peaks.

EXAMPLE 1

Synthesis of (2S)-3-[(3S,4S)-3-[(1R)-1-hydroxy-ethyl]-4-{4-methoxy-3-[(1-pyridin-2-ylazetidin-3-yl)oxy]phenyl}-3-methylpyrrolidin-1-yl]-3-oxopropane-1,2-diol

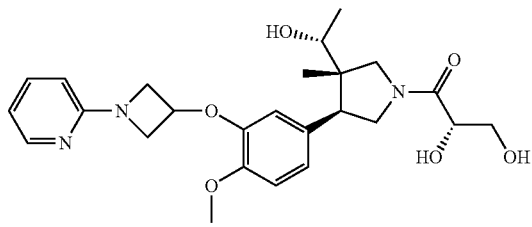 [SMILES: COc1ccc([C@@H]2CN(C(=O)[C@@H](O)CO)C[C@@]2(C)[C@@H](C)O)cc1OC1CN(c2ccccn2)C1]

To a solution of (1R)-1-[(3S,4S)-1-{[(4S)-2,2-dimethyl-1,3-dioxolan-4-yl]carbonyl}-4-(4-methoxy-3-{[1-pyridin-2-ylazetidin-3-yl]oxy}phenyl)-3-methylpyrrolidin-3-yl]ethanol (22.1 mg) in tetrahydrofuran (2 mL) is added aqueous 1.0 M HCl (1 mL). Stir overnight at room temperature. Add aqueous 1.0 M HCl (1 mL) and stir for additional 8 hours. Neutralize with aqueous 1.0 M NaOH, extract with ethyl acetate, dry and evaporate to provide the title compound (18.2 mg). MS(ES+)=472 (M+1).

EXAMPLE 2

Synthesis of (2S)-3-[(3S,4S)-3-[(1R)-1-hydroxy-ethyl]-4-(4-methoxy-3-{[1-(5-methylpyridin-2-yl)azetidin-3-yl]oxy}phenyl)-3-methylpyrrolidin-1-yl]-3-oxopropane-1,2-diol

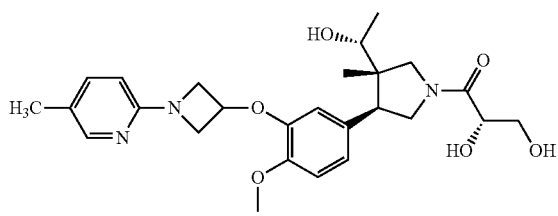 [SMILES: COc1ccc([C@@H]2CN(C(=O)[C@@H](O)CO)C[C@@]2(C)[C@@H](C)O)cc1OC1CN(c2ccc(C)cn2)C1]

The title compound is prepared essentially by the method of Example 1. MS(ES+)=486 (M+1).

EXAMPLE 3

Preparation of crystalline (2S)-3-[(3S,4S)-3-[(1R)-1-hydroxyethyl]-4-(4-methoxy-3-{[1-(5-methylpyridin-2-yl)azetidin-3-yl]oxy}phenyl)-3-methylpyrrolidin-1-yl]-3-oxopropane-1,2-diol An alternative name of (2S)-3-[(3S,4S)-3-[(1R)-1-hydroxyethyl]-4-(4-methoxy-3-{[1-(5-methylpyridin-2-yl)azetidin-3-yl]oxy}phenyl)-3-methylpyrrolidin-1-yl]-3-oxopropane-1,2-diol is (S)-2,3-dihydroxy-1-((3S,4S)-3-((R)-1-hydroxyethyl)-4-(4-methoxy-3-((1-(5-methylpyridin-2-yl)azetidin-3-yl)oxy)phenyl)-3-methylpyrrolidin-1-yl)propan-1-one.

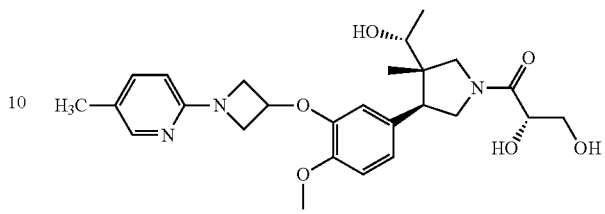

Add (1R)-1-[(3S,4S)-1-{[(4S)-2,2-dimethyl-1,3-dioxolan-4-yl]carbonyl}-4-(4-methoxy-3-{[1-(5-methylpyridin-2-yl)azetidin-3-yl]oxy}phenyl)-3-methylpyrrolidin-3-yl]ethanol (20 g, 38.05 mmol) to a 5-10° C. solution of 1N hydrochloric acid (120 mL, 120.0 mmol). Warm the solution to 20-25° C. and stir for three hours. Add dichloromethane (400 mL) and separate the resulting layers. Add dichloromethane (400 mL) to the aqueous layer and adjust the pH to 7-8 with 7% aqueous sodium bicarbonate. Separate the layers and back extract the aqueous layer with dichloromethane (200 mL). Wash the combined organic layers with water (100 mL). Concentrate the organic layer to dryness. Add ethanol (8 mL) to the title compound (4.0 g). Stir the mixture for twenty hours at 15-20° C. Filter the slurry and dry the wet cake under vacuum to give the title compound as a crystalline solid (3.5 g).

Alternative preparation of crystalline (2S)-3-[(3S,4S)-3-[(1R)-1-hydroxyethyl]-4-(4-methoxy-3-{[1-(5-methylpyridin-2-yl)azetidin-3-yl]oxy}phenyl)-3-methylpyrrolidin-1-yl]-3-oxopropane-1,2-diol.

Add 1N hydrochloric acid (1800 mL, 1.8 mol) to (1R)-1-[(3S,4S)-1-{[(4S)-2,2-dimethyl-1,3-dioxolan-4-yl]carbonyl}-4-(4-methoxy-3-{[1-(5-methylpyridin-2-yl)azetidin-3-yl]oxy}phenyl)-3-methylpyrrolidin-3-yl]ethanol (290 g, 551.7 mmol) at 20-25° C. After stirring for three hours, add dichloromethane (5800 mL) and 10% aqueous sodium carbonate to adjust the pH to 7-8. Add ethanol (1450 mL) and stir the mixture for thirty minutes. Separate the layers and wash the organic layer with water (2900 mL). Concentrate the organic to 2-3 volumes. Add ethanol (1450 mL) and concentrate the organic to 2-3 volumes. Add ethanol (580 mL) and cool the reaction to 15-20° C. Add seed crystals of the title compound (0.1 g) and stir the mixture for twenty-four hours. Filter the slurry and wash the cake with ethanol (290 mL). Dry the cake under vacuum at 55-60° C. for forty hours to yield the title compound (240.0 g, 494.25 mmol): $^1$H NMR (CDCl$_3$) δ 0.73 (m, 3H), 1.19 (d, J=6.0 Hz, 3H), 1.8 (brs, 3H), 2.20 (s, 3H), 3.31 (m, 1H), 3.53 (m, 1H), 3.85 (m, 9H), 4.38 (m, 2H), 4.42 (m, 3H), 5.07 (m, 1H), 6.32 (d, J=8.4 Hz, 1H), 6.68 (d, J=6.0 Hz, 1H), 6.84 (m, 2H), 7.33 (m, 1H), 8.02 (m, 1H); and $^{13}$C-NMR (CDCl$_3$) δ (ppm) 17.0, 17.5, 17.6, 19.6, 44.5, 47.4, 48.8, 49.3, 52.7, 55.9, 57.7, 58.2, 64.0, 64.1, 67.5, 67.6, 67.7, 70.5, 71.3, 106.2, 111.3, 111.4, 115.1, 120.7, 122.1, 128.7, 138.5, 138.7, 145.7, 147.3, 148.1, 158.5, 170.9. Rotational isomerization is observed in the $^1$H and $^{13}$C spectrum, which is causing doubling of relevant peaks.

X-Ray Powder Diffraction

The XRD patterns of crystalline solids are obtained on a Bruker D4 Endeavor X-ray powder diffractometer, equipped with a CuKa source λ=1.54060 Å) and a Vantec detector, operating at 35 kV and 50 mA. The sample is scanned between 4 and 40° in 2θ, with a step size of 0.009° in 2θ and a scan rate of 0.5 seconds/step, and with 0.6 mm divergence, 5.28 fixed anti-scatter, and 9.5 mm detector slits. The dry powder is packed on a quartz sample holder and a smooth surface is obtained using a glass slide. The crystal form diffraction patterns are collected at ambient temperature and relative humidity. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g., The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of °2θ), typically the more prominent peaks. The crystal form diffraction patterns, collected at ambient temperature and relative humidity, were adjusted based on NIST 675 standard peaks at 8.853 and 26.774 degrees 2-theta.

A sample of (2S)-3-[(3S,4S)-3-[(1R)-1-hydroxyethyl]-4-(4-methoxy-3-{[1-(5-methylpyridin-2-yl)azetidin-3-yl]oxy}phenyl)-3-methylpyrrolidin-1-yl]-3-oxopropane-1,2-diol is characterized by an XRD pattern using CuKa radiation as having diffraction peaks (2-theta values) as described in Table 3 below, and in particular having peaks at 18.5° in combination with one or more of the peaks selected from the group consisting of 16.2°, 20.2°, and 14.4°; with a tolerance for the diffraction angles of 0.2 degrees.

TABLE 3

| | Example 3 Peak Positions | |
|---|---|---|
| Peak | Angle° (°2-Theta) +/− 0.2° | Relative Intensity (% of most intense peak) |
| 1 | 13.1 | 21.9 |
| 2 | 24.1 | 22.0 |
| 3 | 25.0 | 27.0 |
| 4 | 22.3 | 30.3 |
| 5 | 20.7 | 32.0 |
| 6 | 19.0 | 45.2 |
| 7 | 14.4 | 46.3 |
| 8 | 20.2 | 50.0 |
| 9 | 16.2 | 86.5 |
| 10 | 18.5 | 100.0 |

We claim:

1. Crystalline (2S)-3-[(3S,4S)-3-[(1R)-1-hydroxyethyl]-4-(4-methoxy-3-{[1-(5-methylpyridin-2-yl)azetidin-3-yl]oxy}phenyl)-3-methylpyrrolidin-1-yl]-3-oxopropane-1,2-diol characterized by an X-ray powder diffraction pattern using CuKα radiation having a diffraction peak at diffraction angle 2-theta of 18.5° in combination with one or more of the peaks selected from the group consisting of 16.2°, 20.2°, and 14.4°; with a tolerance for the diffraction angles of 0.2 degrees.

2. A pharmaceutical composition comprising crystalline (2S)-3-[(3S,4S)-3-[(1R)-1-hydroxyethyl]-4-(4-methoxy-3-{[1-(5-methylpyridin-2-yl)azetidin-3-yl]oxy}phenyl)-3-methylpyrrolidin-1-yl]-3-oxopropane-1,2-diol characterized by an X-ray powder diffraction pattern using CuKα radiation having a diffraction peak at diffraction angle 2-theta of 18.5° in combination with one or more of the peaks selected from the group consisting of 16.2°, 20.2°, and 14.4°; with a tolerance for the diffraction angles of 0.2 degrees, and a pharmaceutically acceptable carrier, diluent or excipient.

* * * * *